United States Patent [19]

Bagli et al.

[11] 4,130,649

[45] Dec. 19, 1978

[54] CYCLOHEPTA[b]PYRIDINE-2-CARBOXYLIC ACID DERIVATIVES

[75] Inventors: Jehan F. Bagli, Kirkland; Tibor Bogri, Montreal, both of Canada

[73] Assignee: Ayerst, McKenna & Harrison Limited, Montreal, Canada

[21] Appl. No.: 789,397

[22] Filed: Apr. 21, 1977

[51] Int. Cl.$^2$ ............................................. A61K 31/455
[52] U.S. Cl. ..................................... 424/266; 544/127; 546/92; 546/183
[58] Field of Search ........... 260/295 F, 295 K, 295 T; 424/263, 266

[56] References Cited

PUBLICATIONS

Chem. Abstracts, 6th Collective Chemical Substances Index, "D-G" 1957-1961, 2H-Furo[2', 3', 5,6,]cyclohepta[1-2, b]pyridine-2-6(3H)-dione, 5H-Cyclohepta[b]pyridine-6,7-dione 5,5-dibromo-8-isopropyl-; and vol. 80, p. 390, paragraph 95687t, 1974.

Primary Examiner—Richard Raymond
Attorney, Agent, or Firm—Stephen Venetianer

[57] ABSTRACT

Cyclohepta[b]pyridine-2-carboxylic acid derivatives characterized by having a 4,7-dihydro-4,7-dioxo-1H-cyclohepta-[b]pyridine nucleus substituted at position 2 with a carboxylic acid or carboxylic acid ester are disclosed. In addition, the nucleus can be optionally further substituted at positions 1, 5,6 and 8. The foregoing compounds are useful for preventing or treating allergic conditions in a mammal. Methods for the preparation and use of the compounds are disclosed.

37 Claims, No Drawings

CYCLOHEPTA [b]PYRIDINE-2-CARBOXYLIC ACID DERIVATIVES

BACKGROUND OF THE INVENTION

1. Field of the Invention

This invention relates to novel cyclohepta[b]pyridine-2-carboxylic acid derivatives, to processes for their preparation, to methods for using said derivatives, and to therapeutically acceptable salts and compositions of said derivatives.

More specifically, the present invention relates to novel 4,7-dihydro-4,7-dioxo-1H-cyclohepta[b]pyridine-2-carboxylic acid derivatives possessing valuable pharmacologic properties. These derivatives are useful for preventing or treating allergic conditions in a mammal at dosages which do not elicit undesirable side effects. The combination of these attributes render the cyclohepta[b]pyridine-2-carboxylic acid derivatives of the invention therapeutically useful.

2. Description of the Prior Art

A number of reports dealing with cyclohepta[b]pyridine derivatives are available. For instance, derivatives of 4,6-dihydroxy-7-oxo-7H-cyclohepta[b]pyridine-3-carboxylic acid are reported by R. Slack and C. F. Attridge, Chemistry and Industry, 471 (1952) and K. Yarmane, Nippon Kageku Zasshi, 81, 295 (1960) see Chem. Abstr., 56, 448e (1962).

The compounds of the present invention are distinguished from the prior art compounds by the nature of the substituents on the cyclohepta[b]pyridine nucleus and by their pharmacologic properties. More specifically, the novel compounds of this invention are distinguished from the prior art compounds by having a carboxylic acid or ester group at position 2 of the cyclohepta[b]pyridine nucleus.

SUMMARY OF THE INVENTION

The compounds of this invention are represented by formula I

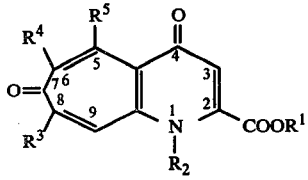

in which $R^1$ is hydrogen or lower alkyl; $R^2$ is hydrogen, lower alkyl, lower alkenyl, lower alkynyl or a radical of formula —Alk—COOR$^6$ wherein Alk is lower alkylene, lower alkenylene or lower alkynylene and $R^6$ is hydrogen or lower alkyl; $R^3$ is hydrogen, bromo, chloro, iodo, lower alkoxy, or phenoxy; $R^4$ is hydroxy, amino, lower alkanoylamino, lower alkoxy, lower alkenyloxy, lower alkynyloxy or a radical of formula —O—Alk—COOR$^6$ wherein Alk and $R^6$ are as defined herein; and $R^5$ is hydrogen, hydroxy, lower alkoxy or phenoxy; or $R^4$ and $R^5$ together form a O—C(CH$_3$)=CH chain having the oxygen atom attached to the carbon atom bearing $R^4$ in formula I; with the proviso that when $R^1$ is hydrogen then $R^6$ is hydrogen.

A preferred group of compounds of this invention are represented by formula I in which $R^1$ is hydrogen or lower alkyl; $R^2$ is hydrogen, lower alkyl, lower alkynyl or a radical of formula —Alk—COOR$^6$ wherein Alk is lower alkylene and $R^6$ is hydrogen or lower alkyl; $R^3$ is hydrogen, bromo or phenoxy; $R^4$ is hydroxy, amino, lower alkanoylamino, lower alkoxy, lower alkynyloxy or a radical of formula —O—Alk—COOR$^6$ wherein Alk is lower alkylene or lower alkenylene and $R^6$ is hydrogen or lower alkyl; and $R^5$ is hydrogen, hydroxy or phenoxy; or $R^4$ and $R^5$ together form a O—C(CH$_3$)=CH chain having the oxygen atom attached to the carbon atom bearing $R^4$ in formula I; with the proviso that when $R^1$ is hydrogen, then $R^6$ is hydrogen.

The therapeutically acceptable salts of the compounds of formula I are also included within the scope of this invention.

The compounds of this invention are prepared by a process comprising:
cyclizing a compound of formula II

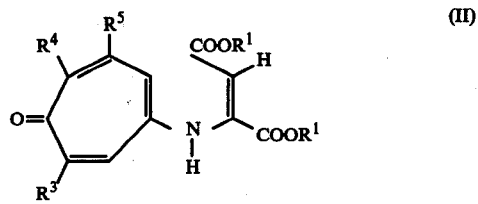

in which $R^1$ is lower alkyl; $R^3$ is hydrogen, lower alkoxy or phenoxy; $R^4$ is hydroxy, amino, lower alkanoylamino or lower alkoxy; and $R^5$ is hydrogen, lower alkoxy or phenoxy to obtain the corresponding compound of formula I in which $R^1$, $R^3$, $R^4$ and $R^5$ are as defined immediately above and $R^2$ is hydrogen; and if desired and required, followed by transformation of the compound of formula I, prepared as described above, to other compounds of formula I by methods described herein.

Another aspect of this invention involves a pharmaceutical composition comprising a compound of formula I, or a therapeutically acceptable addition salt thereof, and a pharmaceutically acceptable carrier.

Still another aspect of this invention involves a method for preventing or treating allergic conditions in a mammal which comprises administering to said mammal an effective allergy alleviating amount of a compound of formula I or a therapeutically acceptable addition salt thereof.

DETAILED DESCRIPTION OF THE INVENTION

The term "lower alkyl" as used herein contemplates straight chain alkyl radicals containing from one to six carbon atoms and branched chain alkyl radicals containing three or four carbon atoms and includes methyl, ethyl, propyl, isopropyl, butyl, isobutyl, pentyl, hexyl and the like.

The term "lower alkoxy" as used herein contemplates straight chain alkoxy radicals containing from one to six carbon atoms and branched chain alkoxy radicals containing three or four carbon atoms and includes methoxy, ethoxy, isopropoxy, butoxy, hexanoxy and the like.

The term "lower alkanoyl" as used herein contemplates straight chain alkanoyl radicals containing from two to six carbon atoms and a branched chain alkanoyl radical containing four carbon atoms and includes acetyl, propionyl, isobutyryl, hexanoyl and the like.

The term "lower alkenyl" as used herein contemplates straight chain alkenyl radicals containing from two to six carbon atoms and branched chain alkenyl radicals containing three or four carbon atoms and includes ethenyl, 2-methyl-2-propenyl, 4-hexenyl and the like.

The term "lower alkynyl" as used herein contemplates straight chain alkynyl radicals containing from two to six carbon atoms and a branched chain alkynyl radical containing four carbon atoms and includes ethynyl, 2-propynyl, 1-methyl-2-propynyl, 3-hexynyl and the like.

The term "(lower)alkylene" as used herein contemplates a divalent organic radical derived from either straight and a branched chain aliphatic hydrocarbons containing from one to six carbon atoms by removal of two hydrogen atoms and includes methylene, ethylene, 1-methylpropylene, 2-ethylpropylene, 2-butylethylene and the like.

The term "(lower)alkenylene" as used herein contemplates a divalent organic radical derived from either straight and branched chain alkene hydrocarbons containing from two to six carbon atoms by removal of two hydrogen atoms and includes ethenylene, 1-propenylene, 2-methyl-2-propenylene, 2-butenylene and the like.

The term "(lower)alkynylene" as used herein contemplates a divalent organic radical derived from either straight and chain alkyne hydrocarbons containing from two to six carbon atoms by removal of two hydrogen atoms and includes ethynylene, 2-propynylene, 1-methyl-2-propynylene, 2-butynylene and the like.

The term "lower alkanol" as used herein contemplates both straight and branched chain alkanols containing from one to four carbon atoms and includes methanol, ethanol, isopropanol, butanol and the like.

The term "lower alkanoic acid" as used herein contemplates straight chain alkanoic acids containing from two to six carbon atoms and a branched chain alkanoic acid containing four carbon atoms and includes acetic acid, 2-methyl-propanoic acid, butanoic acid, hexanoic acid and the like.

The term "inorganic proton acceptor" as used herein contemplates the inorganic bases, preferably the alkali metal hydroxides, carbonates, hydrides, amides and alkoxides, for example, sodium ethoxide, sodium hydroxide, potassium hydroxide, potassium carbonate, sodamide, sodium methoxide, sodium hydride and the like.

The acidic compounds of formula I in which $R^1$ and $R^6$, if present, are hydrogen form salts with suitable therapeutically acceptable inorganic and organic bases. These derived salts possess the same activity as the parent acid and are included within the scope of this invention. The acid is transformed in excellent yield into the corresponding therapeutically acceptable salt by neutralization of said acid with the appropriate inorganic or organic base. The salts are administered in the same manner as the parent acid compounds. Suitable inorganic bases to form these salts include, for example, the hydroxides, carbonates, bicarbonates or alkoxides of the alkali metals or alkaline earth metals, for example, sodium, potassium, magnesium, calcium and the like. Suitable organic bases include the following amines; lower mono-, di- and trialkylamines, the alkyl radicals of which contain up to three carbon atoms, such as methylamine, dimethylamine, trimethylamine, ethylamine, di- and triethylamine, methylethylamine, and the like; mono-, di and trialkanolamines, the alkanol radicals of which contain up to three carbon atoms, for example, mono-, di- and triethanolamine; alkylene-diamines which contain up to six carbon atoms, such as hexamethylenediamine; cyclic saturated or unsaturated bases containing up to six carbon atoms, such as pyrrolidine, piperidine, morpholine, piperazine and their N-alkyl and N-hydroxyalkyl derivatives, such as N-methyl-morpholine and N-(2-hydroxyethyl)-piperidine, as well as pyridine. Furthermore, there may be mentioned the corresponding quaternary salts, such as the tetraalkyl (for example tetramethyl), alkyl-alkanol (for example methyltrimethanol and trimethyl-monoethanol) and cyclic ammonium salts, for example the N-methyl-pyridinium, N-methyl-N-(2-hydroxyethyl)-morpholinium, N,N-dimethylmorpholinium, N-methyl-N-(2-hydroxyethyl)-morpholinium, N,N-dimethyl-piperidinium salts, which are characterized by having good water-solubility. In principle, however, there can be used all the ammonium salts which are physiologically compatible.

The transformations to the salts can be carried out by a variety of methods known in the art. For example, in the case of the inorganic salts, it is preferred to dissolve the acid of formula I in water containing at least one equivalent amount of a hydroxide, carbonate, or bicarbonate corresponding to the inorganic salt desired. Advantageously, the reaction is performed in a water-miscible, inert organic solvent, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, the acid of formula I is dissolved in a suitable solvent of either moderate or lower polarity, for example, ethanol, methanol, ethyl acetate, diethyl ether and benzene. At least an equivalent amount of the amine corresponding to the desired cation is then added to that solution. If the resulting salt does not precipitate, it can usually be obtained in solid form by addition of a miscible diluent of low polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula I with an equivalent amount of the corresponding quaternary ammonium hydroxide in water solution, followed by evaporation of the water.

Since the acidic compounds of formula I can be substituted with two or three acidic groups, these compounds of formula I are capable of forming the di- or tri-salt with two or three equivalents of the base, respectively. The acidic compound of formula I having two or three acidic groups can be reacted with one molar equivalent of a base to form the mono salt of the corresponding compound of formula I. In addition, mixed salts of an acidic compound of formula I can be prepared by reacting the corresponding compound of formula I having two or three acidic groups with one molar equivalent of each of two or three defferent bases, respectively.

The basic compounds of formula I in which $R^4$ is amino form addition salts with suitable inorganic and organic acids. These salts posses the same activities as the parent base compound when administered to a mammal and may be utilized in the same manner. Suitable acids to form these salts include, for example the common mineral acids, hydrohalic, sulfuric or phosphoric, as well as the organic acids, formic, acetic, maleic, malic, citric, or tartaric acid, or acids which are sparingly soluble in body fluids and which impart slow-release properties to their respective salts such as pamoic or tannic acid or carboxymethyl cellulose. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

Also included within the scope of this invention are the isomers of the compounds of formula I resulting from the asymmetric centers contained therein.

Also included within the scope of this invention are the tautomeric forms of the compounds of formula I in which the carbonyl group at positions 4 and/or 7 of the cyclohepta[b]pyridine nucleus is hydroxy resulting from the keto-enol equilibrium contained therein.

Anti-allergic Activity

The compounds of this invention of formula I or therapeutically acceptable salts thereof are useful in the prevention or treatment of allergic reactions in a mammal.

More specifically, the compounds of this invention are useful for the prophylactic treatment as well as for the management of anaphylactic reactions and atopic allergic manifestations, for example, bronchial asthma, hay fever, allergic rhinitis, allergic conjunctivitis, food allergies, urticaria and the like, in a sensitized mammal.

More specifically exemplified, the compounds of this invention are effective anti-allergic agents when tested using the passive cutaneous anaphylaxis (PCA) method, described by I. Mota, Immunology, 7, 681 (1964). The anti-allergic activity of a given compound is measured in rats by its ability to inhibit the increase in vascular permeability at the site of injection of rat immunoglobulin E (igE) followed by i.v. administration of the specific antigen. Evans blue is injected i.v. at the same time as the specific antigen, and the size of the wheal or of the area infiltrated with Evans blue is measured and compared with that of untreated controls. An effective anti-allergic agent will prevent or inhibit the release of inflammatory mediators (mainly serotonin and histamine from the mast cells) which causes an increase in vascular permeability and thus an infiltration of Evans blue surrounding the site of injection of IgE.

The anti-allergic activity of the compounds of formula I is demonstrated by the reduction of the wheal size of sensitized skin tissue compared to that of control animals. A comparison of the anti-allergic activity of the compounds of this invention with the anti-allergic activity of a standard compound, such as disodium cromoglycate, indicates that the compounds of this invention function in the same manner as disodium cromoglycate by blocking the release of mediators from the mast cells responsible for the allergic reaction.

The following representative compounds of this invention are effective anti-allergic agents in rats by reducing the wheal size by at least 50% at intravenous dosages ranging from 0.5 to 3.0 mg per kilogram of body weight: 6-amino-4,7-dihydro-4,7-dioxo-1H-cyclohepta[b]pyridine-2-carboxylic acid (Example 6), 4,7-dihydro-4,7-dioxo-6-methoxy-8-phenoxy-1H-cyclohepta[b]pyridine-2-carboxylic acid (Example 6), 6-acetylamino-4,7-dihydro-4,7-dioxo-1H-cyclohepta[b]pyridine-2-carboxylic acid (Example 6) and 4,7-dihydro-4,7-dioxo-6-(2-propynyloxy)-1H-cyclohepta[b]pyridine-2-carboxylic acid (Example 21).

When the compounds of formula I of this invention are used for suppressing allergic manifestations of anaphylactic reactions and atopic hypersensitivity in a mammal, they are used alone or in combination with pharmacologically acceptable carriers, the proportion of which is determined by the solubility and the chemical nature of the compound, chosen route of administration and standard biological practice. For example, they are administered parenterally by injection; by the nasal route, for instance, as drops or aerosol; or by inhalation from an aerosol.

In addition, the compounds of this invention can be administered in conjunction with common anti-allergics, for example, known compounds effecting anti-histaminic, analgesic, central nervous system depressant, anti-hypertensive, immunosupressive, anti-bradykinin, anti-serotonin or endocrinological responses.

Therapeutic compositions containing the compounds of this invention are effective anti-allergic agents for preventing or relieving anaphylactic allergic manifestations at dosages of 0.1 mg to 100 mg per kilogram of body weight when administered parenterally to a mammal. For administration to a mammal by parenteral injection, it is preferred to use the compounds of formula I in solution in a sterile aqueous vehicle which may also contain other solutes such as buffers or preservatives, as well as sufficient quantities of pharmaceutically acceptable salts or of glucose to make the solution isotonic.

The compounds of formula I can also be administered as nasal powders or insufflations. For such purpose the compounds are administered in finely devided solid form together with a pharmaceutically acceptable solid carrier, for example, a finely divided polyethylene glycol ("Carbowax 1540") or finely divided lactose. Such compositions may also contain other excipients in finely divided solid form, for instance, preservatives, buffers, or surface active agents.

When administering the compounds of this invention by inhalation from an aerosol, the compound of formula I is dissolved in water or ethanol and mixed with a volatile propellant, for example, dichlorotetrafluoroethane and dichlorodifluoromethane, and placed in a pressurized container having a metering valve to release a predetermined amount of material.

The dosage of the compounds of this invention will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstance is reached. In general, the compounds of this invention are most desirably administered at a concentration level that will generally afford effective results without causing any harmful or deleterious side effects, and preferably at a level that is in a range of from about 0.1 mg to about 500 mg per kilogram of body weight per day, although as aforementioned variations will occur. However, a dosage level that is in the range of from about 0.5 mg to about 200 mg per kilogram of body weight per day is most desirably employed in order to achieve effective results.

Processes

Useful and practical starting materials for the preparation of the compounds of this invention of formula I are the tropone derivatives of formula III

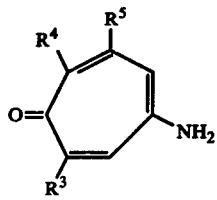

(III)

in which $R^3$ is hydrogen, lower alkoxy or phenoxy; $R^4$ is hydroxy or amino; and $R^5$ is hydrogen, lower alkoxy or phenoxy.

The tropone derivatives of formula III suitable as starting materials are described in a number of reports; for example, see the recent review on tropone derivatives, their preparation and their interconversions by F. Pietra, supra. Thus, the tropone derivatives suitable as starting materials are either known or they can be prepared by conventional means.

The tropone derivatives of formula III are condensed with one to ten molar equivalents, preferably one to two molar equivalents of a di(lower)alkyl acetylenedicarboxylate of formula IV

(IV)

in which $R^1$ is lower alkyl to obtain the corresponding compound of formula II

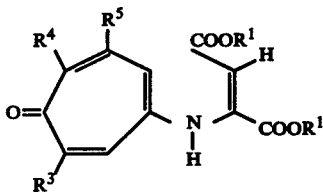

(II)

in which $R^1$, $R^3$, $R^4$ and $R^5$ are as defined immediately above,

In practicing the above condensation it is preferable to use an inert solvent as a reaction medium. Suitable solvents can be selected from the lower alkanols, preferably methanol, ethanol or propanol. Other suitable solvents include dimethylsulfoxide and dimethylformamide. The solvent can be omitted if the reactants are mutually soluble. The condensation is conducted at a temperature in the range from 0° to 100° C., preferably from 10° to 30° C. for 5 to 40 hours, preferably 10 to 20 hours.

The compounds of formula II obtained from the above condensation can be further reacted to obtain other compounds of formula II. For instance, the compound of formula II in which $R^1$, $R^3$ and $R^5$ are as defined immediately above and $R^4$ is hydroxy is alkylated to obtain the corresponding compound of formula II in which $R^1$, $R^3$ and $R^5$ are as defined immediately above and $R^4$ is lower alkoxy. Note that when $R^5$ of formula II is lower alkoxy or phenoxy two isomeric products are obtained due to the tautomeric characteristic of the compound of formula II. The preferred method of alkylation is to react the compound of formula II in which $R^4$ is hydroxy with a molar excess of a diazo(lower)alkane in solution in an inert solvent at a temperature of 0° to 20° C. for 5 minutes to 2 hours. Suitable inert solvents are alkanols (i.e. methanol) and dialkyl ethers (i.e. diethyl ether). Diazo(lower)alkanes useful for this purpose are, for example, diazomethane, diazoethane, 2-diazopropane, 1-diazopentane and the like.

Another useful conversion is to react the compound of formula II in which $R^1$, $R^3$ and $R^5$ are as defined immediately above and $R^4$ is amino with 10 to 50 molar equivalents of an anhydride of a lower alkanoic acid to obtain the corresponding compound of formula II in which $R^1$, $R^3$ and $R^5$ are as defined immediately above and $R^4$ is lower alkanoylamino. Usually the reactants are mutually soluble and a solvent does not have to be used; however if required, an inert solvent can be employed. The reaction is conducted at a temperature of about 0° to 50° C. for 5 to 48 hours.

The above described compounds of formula II are cyclized to obtain the corresponding compound of formula I

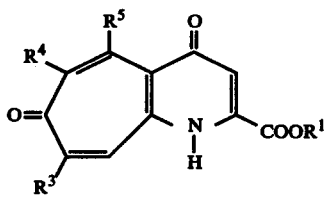

(I)

in which $R^1$ is lower alkyl; $R^2$ is hydrogen; $R^3$ is hydrogen, lower alkoxy or phenoxy; $R^4$ is hydroxy, amino, lower alkanoylamino or lower alkoxy; and $R^5$ is hydrogen, lower alkoxy or phenoxy.

The latter cyclization reaction readily proceeds at a temperature at about 150° to 300° C., preferably 225° to 275° C., for about 5 to 30 hours, preferably 10 to 20 hours. Any inert solvent can be used as a reaction medium and as a practical expedient an inert solvent having a boiling point between 150° to 300° C. is employed. Suitable solvents include diphenyl ether, dimethyl sulfoxide, diethylene glycol, triethylene glycol, glycerine, dibutyl phthalate and the like. Diphenyl ether is the preferred solvent. However, if a melt of the compound of formula II forms, the solvent can be omitted without deleterious effects.

The compound of formula I in which $R^2$ is hydrogen and $R^1$, $R^3$, $R^4$ and $R^5$ are as defined herein may exist in two tautomeric structural forms of formula Ia and Ib which are illustrated below.

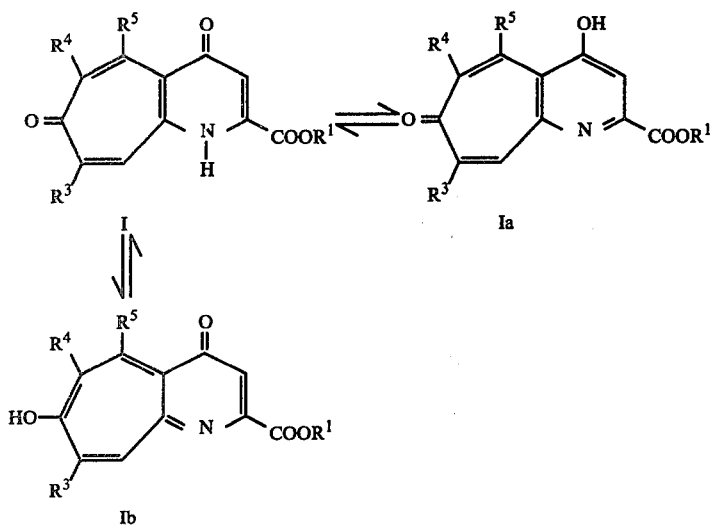

The compounds of formula I obtained from the above described cyclization can be further transformed by chemical reactions to obtain other compounds of formula I by methods described hereinafter.

For instance the compound of formula I in which $R^1$ is lower alkyl; $R^2$ is hydrogen; $R^3$ is hydrogen, lower alkoxy or phenoxy; $R^4$ is hydroxy; and $R^5$ is hydrogen, lower alkoxy or phenoxy can be alkylated to obtain the corresponding compound of formula I in which $R^1$ is lower alkyl; $R^2$ is lower alkyl; $R^3$ is hydrogen, lower alkoxy or phenoxy; $R^4$ is lower alkoxy; and $R^5$ is hydrogen, lower alkoxy or phenoxy. A number of alkylating agents can be employed. The preferred alkylating agent can be selected from a diazo(lower)alkane or di(lower)alkyl sulfate in which the lower alkyl radical contains one or two carbon atoms. Suitable di(lower)sulfates are dimethyl sulfate and diethyl sulfate. The use of a diazo(lower)alkane as an alkylating agent is described above.

A convenient method for alkylating with the di(lower)alkyl sulfate is to stir a mixture of the starting material of formula I with a molar excess (i.e., four to ten molar equivalents) of the di(lower)alkyl sulfate and a similar molar excess of an anhydrous inorganic proton acceptor, preferably potassium carbonate in an inert solvent, preferably a di(lower)alkyl ketone(i.e., 2-propanone, 2-butanone, 3-pentanone and the like) at 50° to 120° C. for 5 to 30 hours.

Another useful conversion of the compound of formula I in which $R^1$ is lower alkyl; $R^2$ is hydrogen; $R^3$ is hydrogen; lower alkoxy or phenoxy; $R^4$ is hydroxy and $R^5$ is hydrogen, lower alkoxy or phenoxy is the reaction of the latter compound with two to ten molar equivalents of a compound of formula Y—X in which Y is lower alkyl, lower alkenyl, lower alkynyl or a radical of formula —Alk—$COOR^6$ wherein Alk is as defined herein and $R^6$ is lower alkyl and X is a halide selected from bromine, chlorine and iodine in the presence of two to ten molar equivalents of an inorganic proton acceptor in an inert solvent to obtain the corresponding compound of formula I in which $R^1$ is lower alkyl; $R^2$ is lower alkyl, lower alkenyl, lower alkynyl or a radical of formula —Alk—$COOR^6$ wherein Alk is as defined herein and $R^6$ is lower alkyl; $R^3$ is hydrogen, lower alkoxy or phenoxy; $R^4$ is lower alkoxy, lower alkenyloxy, lower alkynyloxy or a radical of formula —O—Alk—$COOR^6$ wherein Alk is as defined herein and $R^6$ is lower alkyl; and $R^5$ is hydrogen, lower alkoxy or phenoxy. Suitable inorganic proton acceptors can be selected from sodium hydride, sodium methoxide, sodium hydroxide, potassium t-butoxide, potassium carbonate, and the like and suitable inert solvents can be selected from tetrahydrofuran, dioxane, dimethylformamide, dimethyl sulfoxide and the like. The reaction is conveniently conducted at 10° to 50° C. for 5 hours to 4 days. In this manner compounds of formula I are obtained in which $R^2$ and $R^4$ are both other than hydrogen and hydroxy, respectively, and $R^4$ is identical to "$OR^2$".

The use of one to two molar equivalents of the compound Y—X and/or a shorter period of reaction time, i.e. 1 to 5 hours, gives an easily separable mixture of the corresponding compound of formula I in which $R^1$, $R^3$ and $R^5$ are as defined immediately above, $R^2$ is hydrogen and $R^4$ is lower alkoxy, lower alkenyloxy, lower alkynyloxy or a radical of formula —O—Alk—$COOR^6$ wherein Alk is as defined herein and $R^6$ is lower alkyl and the corresponding compound of formula I in which $R^1$, $R^3$ and $R^5$ are as defined immediately above, $R^2$ is lower alkyl, lower alkenyl, lower alkynyl or a radical of formula —Alk—$COOR^6$ wherein Alk is as defined herein and $R^6$ is lower alkyl and $R^4$ is hydroxy.

Reduction of the above described compound which carry unsaturation in the groups at $R^2$ and/or $R^4$, i.e. compounds of formula I in which $R^1$ is lower alkyl; $R^2$ is hydrogen, lower alkyl, lower alkenyl, lower alkynyl or a radical of formula —Alk—$COOR^6$ wherein Alk is as defined herein and $R^6$ is lower alkyl; $R^3$ is hydrogen, lower alkoxy or phenoxy; $R^4$ is hydroxy, lower alkoxy, lower alkenyl, lower alkynyl or a radical of formula —O—Alk—$COOR^6$ wherein Alk is as defined herein and $R^6$ is lower alkyl; and $R^5$ is hydrogen, lower alkoxy or phenoxy with hydrogen in the presence of a noble metal catalyst, preferably palladium and carbon, in an inert solvent, for example acetic acid, methanol, ethyl acetate, ethanol and the like, gives the corresponding compound of formula I in which $R^1$, $R^3$ and $R^5$ are as defined immediately above; $R^2$ is hydrogen, lower alkyl or a radical of formula —Alk—$COOR^6$ wherein Alk is lower alkylene and $R^6$ is lower alkyl; and $R^4$ is hydroxy, lower alkoxy or a radical of formula —O—Alk—$COOR^6$ wherein Alk is lower alkylene and $R^6$ is lower alkyl.

The compounds of formula I in which $R^3$ is bromo, chloro or iodo are prepared by reacting the compound of formula I in which $R^1$ is lower alkyl, $R^2$ is hydrogen or lower alkyl, $R^3$ is hydrogen, $R^4$ is hydroxy, amino, lower alkanoylamino or lower alkoxy and $R^5$ is hydrogen, lower alkoxy or phenoxy with 1.2 to 4 molar equivalents of bromine, chlorine or iodine in an inert solvent, preferably chloroform, dichloromethane and the like, at 30° to 100° C. or at the boiling point of the solution for 10 to 40 hours to obtain the corresponding compound of formula I in which $R^1$ is lower alkyl; $R^2$ is hydrogen or lower alkyl; $R^3$ is bromo, chloro or iodo; $R^4$ is hydroxy, amino, lower alkanoylamino, or lower alkoxy and $R^5$ is hydrogen, lower alkoxy or phenoxy.

A useful transformation of the compound of formula I in which $R^1$ is lower alkyl; $R^2$ is hydrogen, lower alkyl, lower alkenyl, lower alkynyl or a radical of formula —Alk—COOR$^6$ wherein Alk is as defined herein and $R^6$ is lower alkyl; $R^3$ is hydrogen, lower alkoxy or phenoxy; $R^4$ is 2-propynyloxy and $R^5$ is hydrogen is to heat the latter compound of formula I at 150° to 200° C. for 20 to 80 minutes in an inert solvent, preferably dimethyl sulfoxide, to obtain the corresponding compound of formula I in which $R^1$, $R^2$ and $R^3$ are as defined immediately above and $R^4$ and $R^5$ together form a O—C(CH$_3$) = CH chain. (Note: Some of the compounds of formula I used for this transformation are disclosed hereinafter.) The latter compound of formula I is illustrated by the following structure.

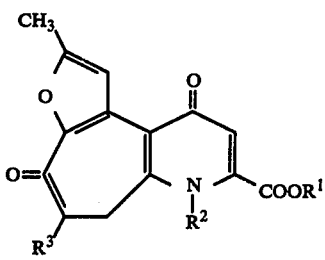

The lower alkoxy group at position 6 of the cyclohepta[b]pyridine nucleus, i.e. the compound of formula I in which $R^4$ is lower alkoxy, can be replaced by another group. For example, the compound of formula I in which $R^1$ is lower alkyl; $R^2$ is hydrogen, lower alkyl, lower alkenyl, lower alkynyl chloro, iodo, or phenoxy; $R^4$ is lower alkoxy; and $R^5$ is hydrogen, at 100° to 130° C. for 1 to 5 hours to obtain the corresponding compound of formula I in which $R^1$, $R^2$, $R^3$ and $R^5$ are as defined immediately above and $R^4$ is 4-morpholinyl.

The above described compounds of formula I having an carboxylic acid ester group in which $R^1$ is lower alkyl and $R^2$ and/or $R^4$ are optionally the radical of formula —Alk—COOR$^6$ or O—Alk—COOR$^6$, respectively, wherein Alk is as defined herein and $R^6$ is lower alkyl, are readily hydrolyzed to obtain the corresponding acidic compounds of formula I, i.e. $R^1$ is hydrogen and $R^6$, if present, is hydrogen. This hydrolysis can be performed under either alkaline or acidic conditions.

A preferred method of alkaline hydrolysis is to react the ester compound of formula I with 1.5 to 10 molar equivalents for each ester group in the molecule of sodium or potassium hydroxide in an inert solvent, preferably water, methanol, ethanol and the like or mixtures thereof. The reaction is maintained at 0° to 40° C. for 5 to 30 hours.

For the acidic hydrolysis, a solution of the compound of formula I having the ester and a 10 to 25 percent aqueous solution of a mineral acid, i.e. sulfuric acid, hydrochloric acid, hydrobromic acid and the like, preferably hydrochloric acid, is heated at 75° to 100° C. or at the boiling point of the reaction mixture for 15 to 120 minutes.

The choice of either alkaline or acidic hydrolysis depends upon whether other substituents present in the particular compound of formula I are affected by the hydrolysis conditions. For example, when the compound of formula I in which $R^2$ is lower alkyl, lower alkenyl, lower alkynyl or a radical of formula —Alk—COOR$^6$ wherein Alk is as defined herein and $R^6$ is lower alkyl is subjected to the above acidic hydrolysis conditions the corresponding compound of formula I in which $R^2$ is hydrogen can be obtained. In some cases, a short time of acidic hydrolysis, for instance 15 to 30 minutes, is sufficient to hydrolyze the ester to the corresponding acid without removing the $R^2$ substituent so that $R^2$ becomes hydrogen. This consideration of the use of acidic hydrolysis is also applicable when $R^3$ and/or $R^5$ is phenoxy, since the phenoxy group can be hydrolyzed under the acidic conditions to obtain the corresponding compound of formula I in which $R^3$ and/or $R^5$ is hydroxy. The use of the above described alkaline conditions for hydrolysis of an ester hydrolyzes only the ester group(s) to the corresponding acid(s) without affecting any of the other substituents attached to the cyclohepta[b]pyridine nucleus.

The acidic compound of formula I in which $R^1$ is hydrogen and optionally $R^2$ is a radical of formula —Alk—COOR$^6$ wherein Alk is as defined herein and $R^6$ is hydrogen and/or $R^4$ is a radical of formula O—Alk—COOR$^6$ wherein Alk is as defined herein and $R^6$ is hydrogen can be esterified using a di(lower)alkyl sulfate or diazo(lower)alkane, in the same manner as described above, to obtain the corresponding compound of formula I in which $R^1$ is lower alkyl and optionally $R^2$ is a radical of formula —Alk—COOR$^6$ wherein Alk is as defined herein and $R^6$ is lower alkyl and/or $R^4$ is a radical of formula —O—Alk—COOR$^6$ wherein Alk is as defined herein and $R^6$ is lower alkyl.

The above described compound of formula I in which $R^1$ is lower alkyl; $R^2$ is hydrogen; $R^3$ is as defined herein; $R^4$ is amino, lower alkanoylamino, lower alkoxy, lower alkenyloxy, lower alkynyloxy or a radical of formula —O—Alk—COOR$^6$ wherein Alk is as defined herein and $R^6$ is lower alkyl and $R^5$ is hydrogen, lower alkoxy or phenoxy; or $R^4$ and $R^5$ together form a O—C(CH$_3$) = CH chain can be alkylated with a di(lower)alkyl sulfate or diazo(lower)alkane or reacted with a compound of formula Y-X wherein X and Y are as defined herein, in the same manner as described above, to obtain the corresponding compound of formula I in which $R^1$, $R^3$, $R^4$ and $R^5$ are as defined immediately above and $R^2$ is lower alkyl, lower alkenyl, lower alkynyl or a radical of formula —Alk—COOR$^6$ wherein Alk is as defined herein and $R^6$ is lower alkyl.

Similarily, the above described compound of formula I in which $R^1$ is lower alkyl; $R^2$ is lower alkyl, lower alkenyl, lower alkynyl or a radical of formula —Alk—COOR$^6$ wherein Alk is as defined herein and $R^6$ is lower alkyl; $R^3$ is as defined herein; $R^4$ is hydroxy; and $R^5$ is hydrogen, lower alkoxy or phenoxy can be alkylated with a di(lower)alkyl sulfate or diazo(lower)alkane or reacted with a compound of formula Y—X wherein X and Y are as defined herein, in the same manner as described above, to obtain the corresponding compound of formula I in which $R^1$, $R^2$, $R^3$ and $R^5$ are as defined immediately above and $R^4$ is lower alkoxy, lower alkenyloxy, lower alkynyloxy or a radical of formula —O—Alk—COOR$^6$ wherein Alk is as defined herein and $R^6$ is lower alkyl.

The following examples illustrate further this invention.

EXAMPLE 1

2-(4-Hydroxy-5-oxo-1,3,6-cycloheptatrien-1-ylamino)-2-butenedioic Acid Diethyl Ester (11; $R^1$ = CH$_2$CH$_3$, $R^3$ and $R^5$ = H and $R^4$ = OH)

A solution of diethyl acetylenedicarboxylate (183.5 g) and 5-amino-2-hydroxy-2,4,6-cycloheptatriene-1-one [147.5 g, described by T. Nozoe et al., Science Repts. Tokoku Univ., First ser., 35, 274(1952)] in ethanol (2,700 ml) is stirred at room temperature for 16 hours. The mixture is filtered and the precipitate is crystallized from ethanol to obtain crystals of the title compound, mp 108.5° C.

In the same manner but replacing 5-amino-2-hydroxy-2,4,6-cycloheptatriene-1-one with an equivalent amount of 2,5-diamino-2,4,6-cycloheptatriene-1-one [described by T. Nozol et al., Science Repts. Tokoku Univ., First ser., 37, 407(1953)], 5-amino-2-hydroxy-3-phenoxy-2,4,6-cycloheptatrien-1-one [described by K. Takase, Bull. Chem. Soc. Japan, 37, 1298(1964)] or 5-amino-2-hydroxy-3-methoxy-2,4,6-cycloheptatrien-1-one, the following compounds of formula II are obtained, respectively: 2-(4-amino-5-oxo-1,3,6-cycloheptatrien-1-ylamino)-2-butenedioic acid diethyl ester, mp 130°-130.5° C., 2-(4-hydroxy-5-oxo-3-phenoxy-1,3,6-cycloheptatrien-1-ylamino)2-butenedioic acid diethyl ester and 2-(4-hydroxy-5-oxo-3-methoxy-1,3,6-cycloheptatrien-1-ylamino)-2-butenedioic acid diethyl ester.

Similarily, replacing diethyl acetylenedicarboxylate with an equivalent amount of dimethyl acetylenedicarboxylate, 2-(4-hydroxy-5-oxo-1,3,6-cycloheptatrien-1-ylamino)-2-butenedioic acid dimethyl ester is obtained.

EXAMPLE 2

2-(4-Methoxy-5-oxo-3-phenoxy-1,3,5-cycloheptatrien-1-ylamino)-2-butenedioic Acid Diethyl Ester (11; $R^1$ = CH$_2$CH$_3$, $R^3$ = OC$_6$H$_5$, $R^4$ = OCH$_3$ and $R^5$ = H)

A solution of diazomethane in ether (i.e., diethyl ethyl) is added to a solution of 2-(4-hydroxy-5-oxo-3-phenoxy-1,3,5-cycloheptatrien-1-ylamino)-2-butenedioic acid diethyl ester (20 g, described in Example 1) in ether (50 ml). After stirring for 15 minutes the solution is evaporated. The residue is subjected to chromatography on silica gel using ether and the eluates are evaporated to give the title compound, mp 55°-70° C., and the corresponding isomer 2-(4-methoxy-5-oxo-6-phenoxy-1,3,5-cycloheptatrien-1-ylamino)-2-butenedioic acid diethyl ester, mp 106°-110° C.

In the same manner but replacing diazomethane with an equivalent amount of 1-diazopropane and replacing 2-(4-hydroxy-5-oxo-3-phenoxy-1,3,5-cycloheptatrien-1-ylamino)-2-butenedioic acid diethyl ester with an equivalent amount of 2-(4-hydroxy-5-oxo-3-methoxy-1,3,6-cycloheptatrien-1-ylamino)-2-butenedioic acid dimethyl ester (described in Example 1), 2-(4-propoxy-5-oxo-3-methoxy-1,3,5-cycloheptatrien-1-ylamino)-2-butenedioic acid dimethyl ester and 2-(4-propoxy-5-oxo-6-methoxy-1,3,5-cycloheptatrien-1-ylamino)-2-butenedioic acid diethyl ester are obtained.

EXAMPLE 3

4,7-Dihydro-4,7-dioxo-6-hydroxy-1H-cyclohepta[b]pyridine-2-carboxylic Acid Ethyl Ester (1; $R^1$ = CH$_2$CH$_3$; $R^2$, $R^3$ and $R^5$ = H and $R^4$ = OH)

2-(4-Hydroxy-5-oxo-1,3,6-cycloheptatrien-1-ylamino)-2-butenedioic acid diethyl ester (100 g, described in Example 1) is added in portions over 5 minutes to diphenyl ether (1000 ml) at reflux temperature. The solution is refluxed for 25 minutes and cooled to room temperature. Hexane (2000 ml) is added and the crystalline precipitate is collected. The precipitate is crystallized from acetic acid to obtain crystals of the title compound, mp > 300° C. and $\nu$ max 3270, 3170, 3100, 1740, 1620 and 1575 cm$^{-1}$.

In the same manner but replacing 2-(4-hydroxy-5-oxo-1,3,6-cycloheptatrien-1-ylamino)-2-butenedioic acid diethyl ester with an equivalent amount of a compound of formula II described in Examples 1 and 2, the following compounds of formula I are obtained, respectively; 6-amino-4,7-dihydro-4,7-dioxo-1H-cyclohepta[b]pyridine-2-carboxylic acid ethyl ester, nmr (trifluoroacetic acid) $\delta$ 1.6 (t, J = 7H$_z$, 3H), 4.8 (q, J = 7H$_z$, 2H) and 7.7 to 8.6 (m, 4H), 4,7-dihydro-4,7-dioxo-6-hydroxy-5-phenoxy-1H-cyclohepta[b]pyridine-2-carboxylic acid ethyl ester, 4,7-dihydro-4,7-dioxo-6-hydroxy-5-methoxy-1H-cyclohepta[b]pyridine-2-carboxylic acid ethyl ester, 4,7-dihydro-4,7-dioxo-6-hydroxy-1H-cyclohepta[b]pyridine-2-carboxylic acid methyl ester, 4,7-dihydro-4,7-dioxo-6-methoxy-5-phenoxy-1H-cyclohepta[b]pyridine-2-carboxylic acid ethyl ester, mp 169°-172° C., 4,7-dihydro-4,7-dioxo-6-methoxy-8-phenoxy-1H-cyclohepta[b]pyridine-2-carboxylic acid ethyl ester, mp 170°-172° C., 4,7-dihydro-4,7-dioxo-6-propoxy-5-methoxy-1H-cyclohepta[b]pyridine-2-carboxylic acid ethyl ester and 4,7-dihydro-4,7-dioxo-6-propoxy-8-methoxy-1H-cyclohepta[b]pyridine-2-carboxylic acid ethyl ester.

EXAMPLE 4

6-Acetylamino-4,7-dihydro-4,7-dioxo-1H-cyclohepta[b]pyridine-2-carboxylic Acid Ethyl Ester (1; $R^1$ = C$_2$H$_5$; $R^2$, $R^3$ and $R^5$ = H and $R^4$ = NHCOCH$_3$)

A solution of 2-(4-amino-5-oxo-1,3,6-cycloheptatrien-1-ylamino)-2-butenedioic acid diethyl ester (1.7 g, described in Example 1) in acetic anhydride (17 ml) is stirred at room temperature for 16 hr. The solution is evaporated and the residue is dissolved in ethyl acetate. The solution is washed with 1N potassium hydroxide and water, dried over sodium sulfate and evaporated to give a residue of 2-(4-acetylamino-5-oxo-1,3,6-cycloheptatrien-1-ylamino)-2-butenedioic acid diethyl ester.

A solution of the latter compound in diphenyl ether (36 ml) is refluxed for 5 minutes and cooled to room temperature. The crystalline precipitate is collected and washed with hexane to obtain the title compound.

EXAMPLE 5

4,7-Dihydro-4,7-dioxo-6-hydroxy-1H-cyclohepta[b]pyridine-2-carboxylic Acid (1; $R^1$, $R^2$, $R^3$ and $R^5$ = H and $R^4$ = OH)

A mixture of 4,7-dihydro-4,7-dioxo-6-hydroxy-1H-cyclohepta[b]pyridine-2-carboxylic acid ethyl ester (2.5 g, described in Example 3) and 19% hydrochloric acid (75 ml) is refluxed for 1 hour and cooled to room temperature. The crystalline precipitate is collected and washed with water, ethanol and ether to obtain the title compound, mp > 270° C.

In the same manner but replacing the above ester with an equivalent amount of 4,7-dihydro-4,7-dioxo-6-methoxy-5-phenoxy-1H-cyclohepta[b]pyridine-2-carboxylic acid ethyl ester (described in Example 3), 4,7-dihydro-4,7-dioxo-5-hydroxy-6-methoxy-1H-cyclohepta[b]pyridine-2-carboxylic acid, mp 258°–260° C., is obtained.

EXAMPLE 6

6-Amino-4,7-dihydro-4,7-dioxo-1H-cyclohepta[b]pyridine-2-carboxylic Acid (1; , $R^1$, $R^2$, $R^3$ and $R^5$ = H and $R^4$ = $NH_2$)

A mixture of 6-amino-4,7-dihydro-4,7-dioxo-1H-cyclohepta[b]pyridine-2-carboxylic acid ethyl ester (0.73 g, described in Example 3) and 2N potassium hydroxide (15 ml) is stirred at room temperature for 16 hr. Hydrochloric acid (10%) is added until the solution is acidic. The crystalline precipitate is collected and washed with water and acetone to give the title compound, mp > 270° C.

In the same manner but replacing the above ester with an equivalent amount of 4,7-dihydro-4,7-dioxo-6-methoxy-5-phenoxy-1H-cyclohepta[b]pyridine-2-carboxylic acid ethyl ester (described in Example 3), 4,7-dihydro-4,7-dioxo-6-hydroxy-5-phenoxy-1H-cyclohepta[b]pyridine-2-carboxylic acid ethyl ester (described in Example 3), 4,7-dihydro-4,7-dioxo-6-hydroxy-5-methoxy-1H-cyclohepta[b]pyridine-2-carboxylic acid ethyl ester (described in Example 3), 4,7-dihydro-4,7-dioxo-6-hydroxy-1H-cyclohepta[b]pyridine-2-carboxylic acid methyl ester (described in Example 3), 4,7-dihydro-4,7-dioxo-6-methoxy-5-phenoxy-1H-cyclohepta[b]pyridine-2-carboxylic acid ethyl ester, (described in Example 3), 4,7-dihydro-4,7-dioxo-6-methoxy-8-phenoxy-1H-cyclohepta[b]pyridine-2-carboxylic acid ethyl ester (described in Example 3), 4,7-dihydro-4,7-dioxo-6-propoxy-5-methoxy-1H-cyclohepta[b]pyridine-2-carboxylic acid ethyl ester (described in Example 3), 4,7-dihydro-4,7-dioxo-6-propoxy-8-methoxy-1H-cyclohepta[b]pyridine-2-carboxylic acid ethyl ester (described in Example 3) or 6-acetylamino-4,7-dihydro-4,7-dioxo-1H-cyclohepta[b]pyridine-2-carboxylic acid ethyl ester (described in Example 4), the following compounds of formula I in which $R^1$ is hydrogen are obtained, respectively; 4,7-dihydro-4,7-dioxo-6-methoxy-5-phenoxy-1H-cyclohepta[b]pyridine-2-carboxylic acid, 4,7-dihydro-4,7-dioxo-6-hydroxy-5-phenoxy-1H-cyclohepta[b]pyridine-2-carboxylic acid, 4,7-dihydro-4,7-dioxo-6-hydroxy-5-methoxy-1H-cyclohepta[b]pyridine-2-carboxylic acid, 4,7-dihydro-4,7-dioxo-6-hydroxy-1H-cyclohepta[b]pyridine-2-carboxylic acid, 4,7-dihydro-4,7-dioxo-6-methoxy-5-phenoxy-1H-cyclohepta[b]pyridine-2-carboxylic acid, mp 222°–224° C., 4,7-dihydro-4,7-dioxo-6-methoxy-8-phenoxy-1H-cyclohepta[b]pyridine-2-carboxylic acid, mp > 250° C., 4,7-dihydro-4,7-dioxo-6-propoxy-5-methoxy-1H-cyclohepta[b]pyridine-2-carboxylic acid, 4,7-dihydro-4,7-dioxo-6-propoxy-8-methoxy-1H-cyclohepta[b]pyridine-2-carboxylic acid and 6-acetylamino-4,7-dihydro-4,7-dioxo-1H-cyclohepta[b]pyridine-2-carboxylic acid, λ max 280 (ε 20,820) and 256 nm (ε 26, 470) and 2-aminoethanol salt, mp > 250° C.

EXAMPLE 7

4,7-Dihydro-4,7-dioxo-6-methoxy-1-methyl-1H-cyclohepta[b]pyridine-2-carboxylic Acid Methyl Ester (1; $R^1$ and $R^2$ = $CH_3$, $R^3$ and $R^5$ = H and $R^4$ = $OCH_3$)

A mixture of 4,7-dihydro-4,7-dioxo-6-hydroxy-1H-cyclohepta[b]pyridine-2-carboxylic acid (2.0 g, described in Example 5), anhydrous potassium carbonate (7.0 g), dimethylsulfate (6.6 g) and 2-butanone (85 ml) is refluxed for 16 hr and filtered while hot. The filtrate is cooled and filtered. The precipitate is dissolved in acetone and the solution is mixed with charcoal, filtered and allowed to crystallize to give crystals of the title compound, mp 219°–221° C.

In the same manner but replacing 4,7-dihydro-4,7-dioxo-6-hydroxy-1H-cyclohepta[b]pyridine-2-carboxylic acid with an equivalent amount of 4,7-dihydro-4,7-dioxo-6-hydroxy-1H-cyclohepta[b]pyridine-2-carboxylic acid ethyl ester (described in Example 3) or 4,7-dihydro-4,7-dioxo-6-propoxy-8-methoxy-1H-cyclohepta[b]pyridine-2-carboxylic acid (described in Example 6), the following compounds of formula I are obtained, respectively; 4,7-dihydro-4,7-dioxo-6-methoxy-1-methyl-1H-cyclohepta[b]pyridine-2-carboxylic acid ethyl ester, mp 181°–183° C., and 4,7-dihydro-4,7-dioxo-6-propoxy-8-methoxy-1-methyl-1H-cyclohepta[b]pyridine-2-carboxylic acid methyl ester.

Similarily, but replacing dimethyl sulfate with diethyl sulfate and replacing 4,7-dihydro-4,7dioxo-6-hydroxy-1H-cyclohepta[b]pyridine-2-carboxylic acid with 4,7-dihydro-4,7-dioxo-6-hydroxy-1H-cyclohepta[b]pyridine-2-carboxylic acid ethyl ester (described in Example 3) or 4,7-dihydro-4,7-dioxo-6-hydroxy-5-phenoxy-1H-cyclohepta[b]pyridine-2-carboxylic acid (described in Example 6), the following compounds of formula I are obtained, respectively; 4,7-dihydro-4,7-dioxo-6-ethoxy-1-ethyl-1H-cyclohepta[b]pyridine-2-carboxylic acid ethyl ester, mp 143°–144° C., and 4,7-dihydro-4,7-dioxo-6-ethoxy-1-ethyl-5-phenoxy-1H-cyclohepta[b]pyridine-2-carboxylic acid ethyl ester.

EXAMPLE 8

4,7-Dihydro-4,7-dioxo-1-methyl-6-(4-morpholinyl)-1H-cyclohepta[b]pyridine-2-carboxylic Acid Ethyl Ester (1; $R^1$ = $CH_2CH_3$, $R^2$ = $CH_3$, $R^3$ and $R^5$ = H and $R^4$ = 4-morpholinyl)

A mixture of 4,7-dihydro-4,7-dihydro-4,7-dioxo-6-methoxy-1-methyl-1H-cyclohepta[b]pyridine-2-carboxylic acid ethyl ester (17 g, described in Example 7) and morpholine (400 ml) is refluxed for 3 hr and evaporated. The residue is subjected to chromatography on silica gel using diethyl ether. The eluates are evaporated and the residue is crystallized from ethyl acetate to obtain crystals of the title compound, mp 170°–172° C.

In the same manner but replacing 4,7-dihydro-4,7-dioxo-6-methoxy-1-methyl-1H-cyclohepta[b]pyridine-2-carboxylic acid ethyl ester with an equivalent amount of 4,7-dihydro-4,7-dioxo-6-methoxy-5-phenoxy-1H-cyclohepta[b]pyridine-2-carboxylic acid (described in Example 6) or 4,7-dihydro-4,7-dioxo-6-methoxy-8-phenoxy-1H-cyclohepta[b]pyridine-2-carboxylic acid ether ester (described in Example 3), the following compounds of formula I are obtained, respectively; 4,7-dihydro-4,7-dioxo-6-(4-morpholinyl)-5-phenoxy-1H-cyclohepta[b]pyridine-2-carboxylic acid and 4,7- dihydro-4,7-dioxo-6-(4-morpholinyl)-8-phenoxy-1H-cyclohepta[b]pyridine-2-carboxylic acid ethyl ester.

EXAMPLE 9

4,7-Dihydro-8-bromo-4,7-dioxo-6-hydroxy-1-methyl-1H-cyclohepta[b]pyridine-2-carboxylic Acid Ethyl Ester (1; $R^1 = CH_2CH_3$, $R^2 = CH_3$, $R^3 = Br$, $R^4 = OH$ and $R^5 = H$)

A solution of 4,7-dihydro-4,7-dioxo-6-methoxy-1-methyl-1H-cyclohepta[b]pyridine-2-carboxylic acid ethyl ester (5.0 g, described in Example 7), 0.5 molar solution of bromine in chloroform (60 ml) and chloroform (50 ml) is refluxed for 16 hr. The precipitate is collected and crystallized from pyridine to obtain crystals of the title compound, mp > 260° C.

In the same manner but replacing bromine with an equivalent amount of chlorine or iodine, 4,7-dihydro-8-chloro-4,7-dioxo-6-hydroxy-1-methyl-1H-cyclohepta[b]pyridine-2-carboxylic acid ethyl ester and 4,7-dihydro-8-iodo-4,7-dioxo-6-hydroxy-1-methyl-1H-cyclohepta[b]pyridine-2-carboxylic acid ethyl ester are obtained, respectively.

Similarly, by replacing 4,7-dihydro-4,7-dioxo-6-methoxy-1-methyl-1H-cyclohepta[b]pyridine-2-carboxylic acid ethyl ester with an equivalent amount of 4,7-dihydro-4,7-dioxo-6-propoxy-5-methoxy-1H-cyclohepta[b]pyridine-2-carboxylic acid (described in Example 6), 4,7-dihydro-4,7-dioxo-6-ethoxy-1-ethyl-5-phenoxy-1H-cyclohepta[b]pyridine-2-carboxylic acid ethyl ester (described in Example 7) or 4,7-dihydro-4,7-dioxo-6-hydroxy-1H-cyclohepta[b]pyridine-2-carboxylic acid ethyl ester (described in Example 3), the following compounds of formula I are obtained, respectively; 4,7-dihydro-8-bromo-4,7-dioxo-6-propoxy-5-methoxy-1H-cyclohepta[b]pyridine-2-carboxylic acid, 4,7-dihydro-8-bromo-4,7-dioxo-6-ethoxy-1-ethyl-5-phenoxy-1H-cyclohepta[b]pyridine-2-carboxylic acid ethyl ester and 4,7-dihydro-8-bromo-4,7-dioxo-6-hydroxy-1H-cyclohepta[b]pyridine-2-carboxylic acid ethyl ester.

EXAMPLE 10

4,7-Dihydro-4,7-dioxo-6-methoxy-1-methyl-1H-cyclohepta[b]pyridine-2-carboxylic Acid (1; $R^1$, $R^3$ and $R^5 = H$, $R^2 = CH_3$ and $R^4 = OCH_3$)

A mixture of 4,7-dihydro-4,7-dioxo-6-methoxy-1-methyl-1H-cyclohepta[b]pyridine-2-carboxylic acid ethyl ester (2.89 g, described in Example 7) and 1N potassium hydroxide (11 ml) is stirred at room temperature for 16 hr. Hydrochloric acid (10%) is added until the solution is acidic. The precipitate is collected, washed with water and acetone and crystallized from acetic acid to obtain crystals of the title compound, mp > 250° C.

In the same manner but replacing 4,7-dihydro-4,7-dioxo-6-methoxy-1-methyl-1H-cyclohepta[b]pyridine-2-carboxylic acid ethyl ester with an equivalent amount of an ester of formula I described in Example 7, the following acids of formula I are obtained, respectively; 4,7-dihydro-4,7-dioxo-6-methoxy-1-methyl-1H-cyclohepta[b]pyridine-2-carboxylic acid, 4,7-dihydro-4,7-dioxo-6-propoxy-8-methoxy-1-methyl-1H-cyclopenta[b]pyridine-2-carboxylic acid, 4,7-dihydro-4,7-dioxo-6-ethoxy-1-ethyl-1H-cyclohepta[b]pyridine-2-carboxylic acid and 4,7-dihydro-4,7-dioxo-6-ethoxy-1-ethyl-5-phenoxy-1H-cyclohepta[b]pyridine-2-carboxylic acid.

EXAMPLE 11

4,7-Dihydro-4,7-dioxo-6-methoxy-1H-cyclopenta[b]pyridine-2-carboxylic Acid (1; $R^1$, $R^2$, $R^3$ and $R^5 = H$ and $R^4 = OCH_3$)

A solution of 4,7-dihydro-4,7-dioxo-6-methoxy-1-methyl-1H-cyclohepta[b]pyridine-2-carboxylic acid ethyl ester (2.0 g, described in Example 7) and 19% hydrochloric acid (60 ml) is refluxed for 30 min. The precipitate is collected and washed with water and acetone to give the title compound. The precipitate is dissolved in aqueous aminoethanol (1M, 4 ml) and acetone (50 ml) is added. The precipitate is collected, washed with acetone and crystallized from water-acetone to give crystals of the aminoethanol salt of the title compound, mp 236°–237° C.

In the same manner but replacing 4,7-dihydro-4,7-dioxo-6-methoxy-1-methyl-1H-cyclohepta[b]pyridine-2-carboxylic acid methyl ester with an equivalent amount of 4,7-dihydro-4,7-dioxo-6-propoxy-8-methoxy-1-methyl-1H-cyclohepta[b]pyridine-2-carboxylic acid methyl ester (described in Example 7) or 4,7-dihydro-4,7-dioxo-6-ethoxy-1-ethyl-5-phenoxy-1H-cyclohepta[b]pyridine-2-carboxylic acid ethyl ester (described in Example 7), the following compounds of formula I are obtained, respectively; 4,7-dihydro-4,7-dioxo-6-propoxy-8-methoxy-1H-cyclohepta[b]pyridine-2-carboxylic acid and 4,7-dihydro-4,7-dioxo-6-ethoxy-5-phenoxy-1H-cyclohepta[b]pyridine-2-carboxylic acid.

EXAMPLE 12

4,7-Dihydro-8-bromo-4,7-dioxo-6-hydroxy-1-methyl-1H-cyclohepta[b]pyridine-2-carboxylic Acid (1; $R^1$ and $R^5 = H$, $R^2 = CH_3$, $R^3 = Br$ and $R^4 = OH$)

A mixture of 4,7-dihydro-8-bromo-4,7-dioxo-6-hydroxy-1-methyl-1H-cyclohepta[b]pyridine-2-carboxylic acid ethyl ester (3.6 g, described in Example 9) and concentrated hydrochloric acid (300 ml) is refluxed for 30 min and cooled to room temperature. The precipitate is collected and washed with water to give the title compound, mp > 250° C.

Similarly, 4,7-dihydro-8-chloro-4,7-dioxo-6-hydroxy-1-methyl-1H-cyclohepta[b]pyridine-2-carboxylic acid ethyl ester (described in Example 9), 4,7-dihydro-8-iodo-4,7-dioxo-6-hydroxy-1-methyl-1H-cyclohepta[b]pyridine-2-carboxylic acid ethyl ester (described in Example 9) and 4,7-dihydro-8-bromo-4,7-dioxo-6-hydroxy-1H-cyclohepta[b]pyridine-2-carboxylic acid ethyl ester (described in Example 9) are hydrolyzed to obtain, respectively; 4,7-dihydro-8-chloro-4,7-dioxo-6-hydroxy-1-methyl-1H-cyclohepta[b]pyridine-2-carboxylic acid, 4,7-dihydro-8-iodo-4,7-dioxo-6-hydroxy-1-methyl-1H-cyclohepta[b]pyridine-2-carboxylic acid and 4,7-dihydro-8-bromo-4,7-dioxo-6-hydroxy-1H-cyclohepta[b]pyridine-2-carboxylic acid.

EXAMPLE 13

4,7-Dihydro-4,7-dioxo-6-ethoxy-1-ethyl-1H-cyclohepta[b]pyridine-2-carboxylic Acid (1; $R^1$, $R^3$ and $R^5 = H$, $R^2 = CH_2CH_3$ and $R^4 = OCH_2CH_3$)

A mixture of 4,7-dihydro-4,7-dioxo-6-ethoxy-1-ethyl-1H-cyclohepta[b]pyridine-2-carboxylic acid ethyl ester (8.2 g, described in Example 7) and 19% hydrochloric acid (246 ml) is refluxed for 30 min and cooled to room temperature. The crystalline precipitate is collected and washed with water to give the title compound, mp 227°–228° C.

EXAMPLE 14

4,7-Dihydro-4,7-dioxo-6-ethoxy-1H-cyclohepta[b]pyridine-2-carboxylic Acid (1; $R^1$, $R^2$, $R^3$ and $R^5$ = H and $R^4$ = OCH$_2$CH$_3$)

A mixture of 4,7-dihydro-4,7-dioxo-6-ethoxy-1-ethyl-1H-cyclohepta[b]pyridine-2-carboxylic acid (5.3 g, described in Example 13) and 19% hydrochloric acid (50 ml) is refluxed for 1 hr and cooled to room temperature. The precipitate is collected and washed with water to give the title compound, mp > 280° C.

EXAMPLE 15

4,7-Dihydro-4,7-dioxo-2-ethoxycarbonyl-6-hydroxy-1H-cyclohepta[b]pyridine-1-acetic Acid Ethyl Ester (1; $R^1$ = CH$_2$CH$_3$, $R^2$ = CH$_2$COOCH$_2$CH$_3$, $R^3$ and $R^5$ = H and $R^4$ = OH)

4,7-Dihydro-4,7-dioxo-6-hydroxy-1H-cyclohepta[b]pyridine-2-carboxylic acid ethyl ester (12.0 g, described in Example 3) is added to a stirring mixture of sodium hydride (57%, 2.8 g) and dimethylformamide (400 ml) at room temperature. Ethyl bromoacetate (15.8 g) is added. The mixture is stirred at room temperature for 20 hr and poured on ice. Water is added and the mixture is extracted with chloroform. The organic extract is dried over sodium sulfate and evaporated. The residue is crystallized from ethyl acetate to give the title compound, mp 186°–188° C.

The mother liquor is subjected to chromatography on silica gel using ether and the eluates are evaporated. The residue is crystallized from acetone-ether to give crystals of 4,7-dihydro-4,7-dioxo-2-ethoxy-carbonyl-6-[(2-ethoxy-2-oxoethyl)oxy]-1H-cyclohepta[b]pyridine-1-acetic acid ethyl ester, mp 93°–95° C.

In the same manner but replacing ethyl bromoacetate with an equivalent amount of ethyl 3-chloropropanate, methyl 4-bromobutanate or ethyl iodide, the following compounds of formula I are obtained, respectively; 4,7-dihydro-4,7-dioxo-2-ethoxycarbonyl-6-hydroxy-1H-cyclohepta[b]pyridine-1-propanoic acid ethyl ester, 4,7-dihydro-4,7-dioxo-2-ethoxycarbonyl-6-[(3-ethoxy-3-oxopropyl)oxy]-1H-cyclohepta[b]pyridine-1-propanoic acid ethyl ester, 4,7-dihydro-4,7-dioxo-2-ethoxycarbonyl-6-hydroxy-1H-cyclohepta[b]pyridine-1-butanoic acid methyl ester, 4,7-dihydro-4,7-dioxo-2-ethoxycarbonyl-6-[(4-ethoxy-4-oxobutyl)oxy]-1H-cyclohepta[b]pyridine-1-butanoic acid methyl ester, 4,7-dihydro-4,7-dioxo-1-ethyl-6-hydroxy-1H-cyclohepta[b]pyridine-2-carboxylic acid ethyl ester and 4,7-dihydro-4,7-dioxo-1-ethyl-6-ethoxy-1H-cyclohepta[b]pyridine-2-carboxylic acid ethyl ester.

EXAMPLE 16

4,7-Dihydro-4,7-dioxo-6-(carboxymethyl)oxy-1H-cyclohepta[b]pyridine-2-carboxylic Acid (1; $R^1$, $R^2$, $R^3$ and $R^5$ = H and $R^4$ = OCH$_2$COOH)

A mixture of 4,7-dihydro-4,7-dioxo-2-ethoxycarbonyl-6-[(2-ethoxy-2-oxoethyl)oxy]-1H-cyclohepta[b]pyridine-1-acetic acid ethyl ester (0.617 g, described in Example 15) and 19% hydrochloric acid (4.2 ml) is refluxed for 1 hr and cooled to room temperature. The precipitate is collected and washed with water, acetone and ether to obtain the title compound, mp > 270° C.

Similarly, replacing the above ester with an equivalent amount of 4,7-dihydro-4,7-dioxo-2-ethoxycarbonyl-6-[(3-methoxy-3-oxo-1-propylpropyl)oxy]-1H-cyclohepta[b]pyridine-1-(3-propylpropanoic acid) methyl ester (described in Example 15), 4,7-dihydro-4,7-dioxo-6-[(2-carboxy-1-propylethyl)oxy]-1H-cyclohepta[b]pyridine-2-carboxylic acid is obtained.

EXAMPLE 17

2-Carboxy-4,7-dihydro-4,7-dioxo-6-hydroxy-1H-cyclopenta[b]pyridine-1-acetic Acid (1; $R^1$, $R^3$ and $R^5$ = H, $R^2$ = CH$_2$COOH and $R^4$ = OH)

A mixture of 4,7-dihydro-4,7-dioxo-2-ethoxycarbonyl-6-hydroxy-1H-cyclohepta[b]pyridine-1-acetic acid ethyl ester (1.7 g, described in Example 15) and 1N potassium hydroxide (12 ml) is stirred at room temperature for 2.5 hr. Hydrochloric acid (19%) is added until the mixture is acidic. The precipitate is collected and washed with water, acetone and ether to obtain the title compound, mp > 270° C.

Similarly, replacing the above ester with an equivalent amount of 4,7-dihydro-4,7-dioxo-2-ethoxycarbonyl-6-hydroxy-1H-cyclohepta[b]pyridine-1-propanoic acid ethyl ester (described in Example 15) or 4,7-dihydro-4,7-dioxo-2-ethoxycarbonyl-6-hydroxy-1H-cyclohepta[b]pyridine-1-butanoic acid methyl ester (described in Example 15), 2-carboxy-4,7-dihydro-4,7-dioxo-6-hydroxy-1H-cyclohepta[b]pyridine-1-propanoic acid and 2-carboxy-4,7-dihydro-4,7-dioxo-6-hydroxy-1H-cyclohepta[b]pyridine-1-butanoic acid are obtained, respectively.

EXAMPLE 18

2-Carboxy-4,7-dihydro-4,7-dioxo-6-(carboxymethyl)oxy-1H-cyclohepta[b]pyridine-1-acetic acid (1; $R^1$, $R^3$ and $R^5$ = H, $R^2$ = CH$_2$COOH and $R^4$ = OCH$_2$—COOH)

A mixture of 4,7-dihydro-4,7-dioxo-2-ethoxycarbonyl-6-[(2-ethoxy-2-oxoethyl)oxy]-1H-cyclohepta[b]pyridine-1-acetic acid ethyl ester (1.72 g, described in Example 15) and 2N potassium hydroxide (12 ml) is stirred at room temperature for 2.5 hr and 19% hydrochloric acid is added until the mixture is acidic. The precipitate is collected and washed with water, acetone and ether to obtain the title compound. The precipitate is dissolved in aqueous aminoethanol (1M, 4 ml) and acetone (50 ml is added). The precipitate is collected, washed with acetone and crystallized from water-acetone to give crystals of the aminoethanol salt of the title compound, mp 236°–237° C.

In the same manner but replacing the above ester with an equivalent amount of 4,7-dihydro-4,7-dioxo-2-ethoxycarbonyl-6-[(3-ethoxy-3-oxopropyl)oxy]-1H-cyclohepta[b]pyridine-1-propanoic acid ethyl ester (described in Example 15) or 4,7-dihydro-4,7-dioxo-2-ethoxy-carbonyl-6[(3-methoxy-3-oxo-1-propylpropyl)oxy]-1H-cyclohepta[b]pyridine-1-(3-propylpropanoic acid) methyl ester, 2-carboxy-4,7-dihydro-4,7-dioxo-6-[(2-carboxy-ethyl)oxy]-1H-cyclohepta[b]pyridine-1-propanoic acid and 2-carboxy-4,7-dihydro-4,7-dioxo-6-[(2-carboxy-1-propylethyl)oxy]-1H-cyclohepta[b]pyridine-1-(3-propylpropanoic acid) are obtained, respectively.

EXAMPLE 19

4,7-Dihydro-4,7-dioxo-6-[(4-ethoxy-4-oxo-2-buten-1-yl)oxy]-1H-cyclohepta[b]pyridine-2-carboxyl Acid Ethyl Ester (1; $R^1$ = $CH_2CH_3$, $R^2$, $R^3$ and $R^5$ = H and $R^4$ = $OCH_2CH = CHCOOCH_2CH_3$)

4-Bromo-2-butenoic acid ethyl ester (5.2 g) is added to a mixture of 4,7-dihydro-4,7-dioxo-6-hydroxy-1H-cyclohepta[b]pyridine-2-carboxylic acid ethyl ester (2.61 g, described in Example 3), sodium hydride (57%, 0.63 g) and dimethylformamide (100 ml) at room temperature and the mixture is stirred at room temperature for 2.5 days. The mixture is poured on ice, water is added and the mixture is extracted with chloroform. The organic extract is dried over sodium sulfate and evaporated. The residue is crystallized from ethyl acetate to obtain crystals of the title compound, mp 203°-205° C. The mother liquors are subjected to chromatography on silica gel using ether and the eluates are evaporated to obtain 4,7-dihydro-4,7-dioxo-6-[(4-ethoxy-4-oxo-2-buten-1-yl)oxy]-1-(4-ethoxy-4-oxo-2-buten-1-yl)-1H-cyclohepta[b]pyridine-2-carboxylic acid ethyl ester.

Similarly, replacing 4-bromo-2-butenoic acid ethyl ester with an equivalent amount of 4-chloro-2-butynoic acid methyl ester, 6-bromo-3-hexynoic acid ethyl ester or 5-chloro-b 2-methyl-3-propenoic acid methyl ester, the following compounds of formula I are obtained, respectively; 4,7-dihydro-4,7-dioxo-6-[(4-methoxy-4-oxo-2-butyn-1-yl)oxy]-1H-cyclohepta[b]pyridine-2-carboxylic acid ethyl ester, 4,7-dihydro-4,7-dioxo-6-[(4-methoxy-4-oxo-2-butyn-1-yl)oxy]-1-(4-methoxy-4-oxo-2-butyn-1-yl)-1H-cyclohepta[b]pyridine-2-carboxylic acid ethyl ester, 4,7-dihydro-4,7-dioxo-6-[(6-ethoxy-6-oxo-3-hexyn-1-yl)oxy]-1H-cyclohepta[b]pyridine-2-carboxylic acid ethyl ester, 4,7-dihydro-4,7-dioxo-6-[(6-ethoxy-6-oxo-3-hexyn-1-yl)oxy]-1-(6-ethoxy-6-oxo-3-hexyn-1-yl)-1H-cyclohepta[b]pyridine-2-carboxylic acid ethyl ester, 4,7-dihydro-4,7-dioxo-6-[(5-methoxy-5-oxo-4-methyl-2-penten-1-yl)oxy]-1H-cyclohepta[b]pyridine-2-carboxylic acid ethyl ester and 4,7-dihydro-4,7-dioxo-6-[(5-methoxy-5-oxo-4-methyl-2-penten-1-yl)-oxy]-1-(5-methoxy-5-oxo-4-methyl-2-penten-1-yl)-1H-cyclohepta[b]pyridine-2-carboxylic acid ethyl ester.

EXAMPLE 20

4,7-Dihydro-4,7-dioxo-1-(2-propynyl)-6-(2-propynyloxy)-1H-cyclohepta[b]pyridine-2-carboxylic acid ethyl ester (1; $R^1$ = $CH_2CH_3$, $R^2$ = $CH_2C\equiv CH$, $R^3$ and $R^5$ = H and $R^4$ = $OCH_2O\equiv CH$)

A mixture of 4,7-dihydro-4,7-dioxo-6-hydroxy-1H-cyclohepta[b]pyridine-2-carboxylic acid ethyl ester (3.41 g, described in Example 3), potassium carbonate (5.4 g), 2-propynyl bromide (4.66 g) and dimethylsulfoxide (65 ml) is stirred at room temperature for 16 hr. Water (260 ml) is added and the mixture is extracted with dichloromethane. The organic extract is washed with water dried over sodium sulfate and evaporated. The residue is crystallized from ethanol to obtain crystals of the title compound, mp 169° C. The mother liquors obtained from the crystallization are subjected to chromatography on silica gel using ether and the eluates are evaporated to give 4,7-dihydro-4,7-dioxo-6-hydroxy-1-(2-propenyl)-1H-cyclohepta[b]pyridine-2-carboxylic acid ethyl ester.

In the same manner but replacing 2-propynyl bromide with an equivalent amount of 2-butenyl bromide, 3-methylbutyl chloride or 3-pentynyl bromide the following compounds of formula 1 are obtained, respectively; 4,7-dihydro-4,7-dioxo-1-(2-butenyl)-6-(2-butenyloxy)-1H-cyclohepta[b]pyridine-2-carboxylic acid ethyl ester, 4,7-dihydro-4,7-dioxo-6-hydroxy-1-(2-butenyl)-1H-cyclohepta[b]pyridine-2-carboxylic acid ethyl ester, 4,7-dihydro-4,7-dioxo-1-(3-methylbutyl)-6-(3-methyl-butyloxy)-1H-cyclohepta[b]pyridine-2-carboxylic acid ethyl ester, 4,7-dihydro-4,7-dioxo-6-hydroxy-1-(3-methylbutyl)-1H-cyclohepta[b]pyridine-2-carboxylic acid ethyl ester, 4,7-dihydro-4,7-dioxo-1-(3-pentynyl)-6-(3-pentynyloxy)-1H-cyclohepta[b]pyridine-2-carboxylic acid ethyl ester and 4,7-dihydro-4,7-dioxo-6-hydroxy-1-(3-pentynyl)-1H-cyclohepta[b]pyridine-2-carboxylic acid ethyl ester.

EXAMPLE 21

4,7-Dihydro-4,7-dioxo-6-(2-propynyloxy)-1H-cyclohepta[b]pyridine-2-carboxylic Acid (1; $R^1$, $R^2$, $R^3$ and $R^5$ = H and $R^4$ = $OCH_2C = CH$)

A mixture of 4,7-dihydro-4,7-dioxo-1-(2-propynyl)-6-(2-propynyloxy)-1H-cyclohepta[b]pyridine-2-carboxylic Acid ethyl ester (2.0 g, described in Example 20) and 19% hydrochloric acid (59 ml) is refluxed for 30 minutes and cooled to room temperature. The crystalline precipitate is collected and dried to obtain the title compound, mp 189° (darkens) and 250° C. (dec).

Similarly, replacing the above ester with an equivalent amount of 4,7-dihydro-4,7-dioxo-1-(2-butenyl)-6-(2-butenyloxy)-1H-cyclohepta[b]pyridine-2-carboxylic acid ethyl ester (described in Example 20), 4,7-dihydro-4,7-dioxo-1-(3-methylbutyl)-6-(3-methylbutyloxy)-1H-cyclohepta[b]pyridine-2-carboxylic acid ethyl ester (described in Example 20) or 4,7-dihydro-4,7-dioxo-1-(3-pentynyl)-6-(3-pentynyloxy)-1H-cyclohepta[b]pyridine-2-carboxylic acid ethyl ester (described in Example 20), the following compounds of formula 1 are obtained, respectively; 4,7-dihydro-4,7-dioxo-6-(2-butenyloxy)-1H-cyclohepta[b]pyridine-2-carboxylic acid 4,7-dihydro-4,7-dioxo-6-(3-methylbutyloxy)-1H-cyclohepta[b]pyridine-2-carboxylic acid and 4,7-dihydro-4,7-dioxo-6-(3-pentynyloxy)-1H-cyclohepta[b]pyridine-2-carboxylic acid.

EXAMPLE 22

4,7-Dihydro-4,7-dioxo-6-propoxy-1-propyl-1H-cyclohepta[b]pyridine-2-carboxylic Acid Ethyl Ester (1; $R^1$ = $CH_2CH_3$, $R^2$ = $CH_2CH_2CH_3$, $R^3$ and $R^5$ = H and $R^4$ = $OCH_2CH_2CH_3$)

A mixture of 4,7-dihydro-4,7-dioxo-1-(2-propynyl)-6-(2-propynyloxy)-1H-cyclohepta[b]pyridine-2-carboxylic acid ethyl ester (20 g, described in Example 20), 5% palladium on charcoal (2.0 g) and acetic acid (400 ml) is stirred rapidly under an atmosphere of hydrogen until 5.7 liters of hydrogen are absorbed. The mixture is filtered and the filtrate is evaporated. The residue is subjected to chromatography on silica gel using acetone-hexane (1:1). The eluates are evaporated to give a residue of the title compound.

EXAMPLE 23

4,7-Dihydro-4,7-dioxo-6-propoxy-1H-cyclohepta[b]pyridine-2-carboxylic acid (1; $R^1$, $R^2$, $R^3$ and $R^5$ = H and $R^4$ = $OCH_2CH_2CH_3$)

A mixture of 4,7-dihydro-4,7-dioxo-6-propoxy-1-propyl-1H-cyclohepta[b]pyridine-2-carboxlic acid ethyl ester (3.8 g, described in Example 22) and 19% hydrochloric acid (113 ml) is refluxed for 30 minutes. Charcoal is added and the hot mixture is filtered. The filtrate is cooled to room temperature and the crystalline precipitate is collected and dried to obtain the title compound, mp > 250° C.

EXAMPLE 24

7,10-Dihydro-4,10-dioxo-2-methyl-7-propynyl-4H-furo[3′,2′: 3,4]-cyclohepta[1,2-b]pyridine-6-carboxylic Acid Ethyl Ester (1; $R^1$ = $CH_2CH_3$, $R^2$ = $CH_2C \equiv CH$, $R^3$ = H and $R^4$ and $R^5$ together is O—C($CH_3$)=CH)

A solution of 4,7-dihydro-4,7-dioxo-1-(2-propynyl)-6-(2-propynyloxy)-1H-cyclohepta[b]pyridine-2-carboxylic acid ethyl ester (1.0 g, described in Example 20) and dimethylsulfoxide (20 ml) is heated at 175° C. for 40 minutes and cooled to room temperature. Water (200 ml) is added and the solution is extracted with ethyl acetate. The organic extract is washed with water, dried over sodium sulfate, concentrated to 50 ml and cooled to 0° C. The crystals are collected and subjected to chromatography on silica gel using ether. The eluates are evaporated and the residue is crystallized from ethyl acetate to obtain crystals of the title compound, mp 185°–186° C.

EXAMPLE 25

7,10-Dihydro-4,10-dioxo-2-methyl-7-propynyl-4H-furo[3′,2′: 3,4]-cyclohepta[1,2-b]pyridine-6-carboxylic Acid (1; $R^1$ and $R^3$ = H, $R^2$ = $CH_2C \equiv CH$ and $R^4$ and $R^5$ together is O—C($CH_3$)=CH)

A mixture of 7,10-dihydro-4,10-dioxo-2-methyl-7-propynyl-4H-furo[3′,2′: 3,4]cyclohepta[1,2-b]pyridine-6-carboxylic acid ethyl ester (1.2 g, described in Example 24), 1N potassium hydroxide (4 ml) and water (6 ml) is stirred at room temperature for 16 hr. The precipitate is removed and the solution is acidified with 10% hydrochloric acid. The precipitate is collected, washed with water and crystallized from pyridine to obtain crystals of the title compound, mp 237°–238° C.

In the same manner the esters described in Example 20 are hydrolyzed under the above alkaline conditions to obtain, respectively; 4,7-dihydro-4,7-dioxo-1-(2-propynyl)-6-(2-propynyloxy)-1H-cyclohepta[b]pyridine-2-carboxylic acid, 4,7-dihydro-4,7-dioxo-6-hydroxy-1-(2-propynyl)-1H-cyclohepta[b]pyridine-2-carboxylic acid, 4,7-dihydro-4,7-dioxo-1-(2-butenyl)-6-(2-butenyloxy)-1H-cyclohepta[b]pyridine-2-carboxylic acid, 4,7-dihydro-4,7-dioxo-6-hydroxy-1-(2-butenyl)-1H-cyclohepta[b]pyridine-2-carboxylic acid, 4,7-dihydro-4,7-dioxo-1-(3-methylbutyl)-6-(3-methylbutyloxy)-1H-cyclohepta[b]pyridine-2-carboxylic acid, 4,7-dihydro-4,7-dioxo-6-hydroxy-1-(3-methylbutyl)-1-H-cyclohepta[b]pyridine-2-carboxylic acid, 4,7-dihydro-4,7-dioxo-1-(3-pentynyl)-6-(3-pentynyloxy)-1H-cyclohepta[b]pyridine-2-carboxylic acid and 4,7-dihydro-4,7-dioxo-6-hydroxy-1-(3-pentynyl)-1H-cyclohepta[b]pyridine-2-carboxylic acid.

EXAMPLE 26

7,10-Dihydro-4,10-dioxo-2-methyl-4H-furo[3′,2′: 3,4]cyclohepta[1,2-b]pyridine-6-carboxylic Acid (1; $R^1$, $R^2$ and $R^3$ = H and $R^4$ and $R^5$ together is OC($CH_3$)=CH)

A mixture of 7,10-dihydro-4,10-dioxo-2-methyl-7-propynyl-4H-furo[3′, 2′: 3,4]cyclohepta[1,2-b]pyridine-6-carboxylic acid ethyl ester (2.0 g, described in Example 24) and 19% hydrochloric acid (60 ml) is refluxed for 45 minutes and cooled to room temperature. The precipitate of the title compound is collected, washed with acetone and crystallized from pyridine to obtain crystals of the pyridine salt of the title compound, mp 292°–295° C.

We claim:

1. A compound of the formula

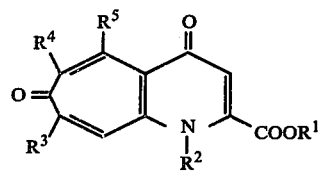

in which $R^1$ is hydrogen or lower alkyl; $R^2$ is hydrogen, lower alkyl, lower alkenyl, lower alkynyl or a radical of formula —Alk—COOR$^6$ wherein Alk is lower alkylene, lower alkenylene or lower alkynylene and $R^6$ is hydrogen or lower alkyl; $R^3$ is hydrogen, bromo, chloro, iodo, lower alkoxy or phenoxy; $R^4$ is hydroxy, amino, lower alkanoylamino, lower alkoxy, lower alkenyloxy, lower alkynyloxy or a radical of formula —O—Alk—COOR$^6$ wherein Alk is lower alkylene, lower alkenylene or lower alkynylene and $R^6$ is hydrogen or lower alkyl; and $R^5$ is hydrogen, hydroxy, lower alkoxy or phenoxy; $R^4$ and $R^5$ together form a O—C($CH_3$)=CH chain having the oxygen atom attached to the carbon atom bearing $R^4$; with the proviso that when $R^1$ is hydrogen then $R^6$ is hydrogen; or a therapeutically acceptable salt thereof.

2. A compound of the formula

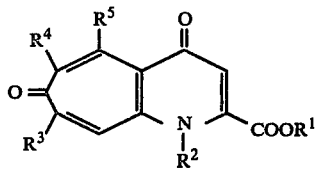

in which $R^1$ is hydrogen or lower alkyl; $R^2$ is hydrogen, lower alkyl, lower alkynyl or a radical of formula —Alk—COOR$^6$ wherein Alk is lower alkylene and $R^6$ is hydrogen or lower alkyl; $R^3$ is hydrogen, bromo or phenoxy; $R^4$ is hydroxy, amino, lower alkanoylamino, lower alkoxy, lower alkynyloxy or a radical of formula —O—Alk—COOR$^6$ wherein Alk is lower alkylene or lower alkenylene and $R^6$ is hydrogen or lower alkyl; and $R^5$ is hydrogen, hydroxy or phenoxy; or $R^4$ and $R^5$ together form a O—C($CH_3$)=CH chain having the oxygen atom attached to the carbon atom bearing $R^4$; with the proviso that when $R^1$ is hydrogen then $R^6$ is hydrogen or a therapeutically acceptable salt thereof.

3. 4,7-Dihydro-4,7-dioxo-6-hydroxy-1H-cyclohepta[b]pyridine-2-carboxylic acid ethyl ester, as claimed in claim 1.

4. 6-Amino-4,7-dihydro-4,7-dioxo-1H-cyclohepta[b]pyridine-2-carboxylic acid ethyl ester, as claimed in claim 1.

5. 4,7-Dihydro-4,7-dioxo-6-methoxy-8-phenoxy-1H-cyclohepta[b]pyridine-2-carboxylic acid ethyl ester, as claimed in claim 1.

6. 4,7-Dihydro-4,7-dioxo-6-methoxy-5-phenoxy-1H-cyclohepta[b]pyridine-2-carboxylic acid ethyl ester, as claimed in claim 1.

7. 6-Acetylamino-4,7-dihydro-4,7-dioxo-1H-cyclohepta[b]pyridine-2-carboxylic acid ethyl ester, as claimed in claim 1.

8. 4,7-Dihydro-4,7-dioxo-6-hydroxy-1H-cyclohepta[b]pyridine-2-carboxylic acid, as claimed in claim 1.

9. 4,7-Dihydro-4,7-dioxo-5-hydroxy-6-methoxy-1H-cyclohepta[b]pyridine-2-carboxylic acid, as claimed in claim 1.

10. 6-Amino-4,7-dihydro-4,7-dioxo-1H-cyclohepta[b]pyridine-2-carboxylic acid, as claimed in claim 1.

11. 4,7-Dihydro-4,7-dioxo-6-methoxy-5-phenoxy-1H-cyclohepta[b]pyridine-2-carboxylic acid, as claimed in claim 1.

12. 4,7-Dihydro-4,7-dioxo-6-methoxy-8-phenoxy-1H-cyclohepta[b]pyridine-2-carboxylic acid, as claimed in claim 1.

13. 6-Acetylamino-4,7-dihydro-4,7-dioxo-1H-cyclohepta[b]pyridine-2-carboxylic acid, as claimed in claim 1.

14. 4,7-Dihydro-4,7-dioxo-6-methoxy-1-methyl-1H-cyclohepta[b]pyridine-2-carboxylic acid methyl ester, as claimed in claim 1.

15. 4,7-Dihydro-4,7-dioxo-6-methoxy-1-methyl-1H-cyclohepta[b]pyridine-2-carboxylic acid ethyl ester, as claimed in claim 1.

16. 4,7-Dihydro-4,7-dioxo-6-ethoxy-1-ethyl-1H-cyclohepta[b]pyridine-2-carboxylic acid ethyl ester, as claimed in claim 1.

17. 4,7-Dihydro-8-bromo-4,7-dioxo-6-hydroxy-1-methyl-1H-cyclohepta[b]pyridine-2-carboxylic acid ethyl ester, as claimed in claim 1.

18. 4,7-Dihydro-4,7-dioxo-6-methoxy-1-methyl-1H-cyclohepta[b]pyridine-2-carboxylic acid, as claimed in claim 1.

19. 4,7-Dihydro-4,7-dioxo-6-methoxy-1H-cyclohepta[b]pyridine-2-carboxylic acid, as claimed in claim 1.

20. 4,7-Dihydro-4,7-dioxo-6-hydroxy-1-methyl-1H-cyclohepta[b]pyridine-2-carboxylic acid, as claimed in claim 1.

21. 4,7-Dihydro-4,7-dioxo-6-ethoxy-1-ethyl-1H-cyclohepta[b]pyridine-2-carboxylic acid, as claimed in claim 1.

22. 4,7-Dihydro-4,7-dioxo-6-ethoxy-1H-cyclohepta[b]pyridine-2-carboxylic acid, as claimed in claim 1.

23. 4,7-Dihydro-4,7-dioxo-2-ethoxycarbonyl-6-hydroxy-1H-cyclohepta-[b]pyridine-1-acetic acid ethyl ester, as claimed in claim 1.

24. 4,7-Dihydro-4,7-dioxo-2-ethoxycarbonyl-6-[(2-ethoxy-2-oxoethyl)oxy]-1H-cyclohepta[b]pyridine-1-acetic acid ethyl ester, as claimed in claim 1.

25. 4,7-Dihydro-4,7-dioxo-6-(carboxymethyl)oxy-1H-cyclohepta[b]pyridine-2-carboxylic acid, as claimed in claim 1.

26. 2-Carboxy-4,7-dihydro-4,7-dioxo-6-hydroxy-1H-cyclohepta[b]pyridine-1-acetic acid, as claimed in claim 1.

27. 2-Carboxy-4,7-dihydro-4,7-dioxo-6-(carboxymethyl)oxy-1H-cyclohepta[b]pyridine-1-acetic acid, as claimed in claim 1.

28. 4,7-Dihydro-4,7-dioxo-6-[(4-ethoxy-4-oxo-2-buten-1-yl)-oxy]-1H-cyclohepta[b]pyridine-2-carboxylic acid ethyl ester, as claimed in claim 1.

29. 4,7-Dihydro-4,7-dioxo-1-(2-propynyl)-6-(2-propynyloxy)-1H-cyclohepta[b]pyridine-2-carboxylic acid ethyl ester, as claimed in claim 1.

30. 4,7-Dihydro-4,7-dioxo-6-(2-propynyloxy)-1H-cyclohepta[b]pyridine-2-carboxylic acid, as claimed in claim 1.

31. 4,7-Dihydro-4,7-dioxo-6-propoxy-1-propyl-1H-cyclohepta[b]pyridine-2-carboxylic acid ethyl ester, as claimed in claim 1.

32. 4,7-Dihydro-4,7-dioxo-6-propoxy-1H-cyclohepta[b]pyridine-2-carboxylic acid, as claimed in claim 1.

33. 7,10-Dihydro-4,10-dioxo-2-methyl-7-propynyl-4H-furo[3',2': 3,4]cyclohepta[1,2-b]pyridine-6-carboxylic acid ethyl ester, as claimed in claim 1.

34. 7,10-Dihydro-4,10-dioxo-2-methyl-7-propynyl-4H-furo[3',2': 3,4]cyclohepta[b]pyridine-6-carboxylic acid, as claimed in claim 1.

35. 7,10-Dihydro-4,10-dioxo-2-methyl-4H-furo[3',2': 3,4]cyclohepta[1,2-b]pyridine-6-carboxylic acid, as claimed in claim 1.

36. A method for preventing or treating allergic conditions in a mammal which comprises administering to said mammal an effective allergy alleviating amount of a compound of claim 1, or a therapeutically acceptable salt thereof.

37. A pharmaceutical composition comprising an effective allergy alleviating amount of a compound of claim 1, or a therapeutically acceptable salt thereof, and a pharmaceutically acceptable carrier.

* * * * *